United States Patent
Hall et al.

(10) Patent No.: US 12,064,579 B2
(45) Date of Patent: *Aug. 20, 2024

(54) APPARATUS FOR TOPICAL NEGATIVE PRESSURE THERAPY

(71) Applicant: Smith & Nephew PLC, Watford (GB)

(72) Inventors: Kristian Hall, Hessle (GB); Edward Yerbury Hartwell, Hull (GB)

(73) Assignee: Smith & Nephew PLC, Watford (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/220,159

(22) Filed: Jul. 10, 2023

(65) Prior Publication Data
US 2023/0347118 A1    Nov. 2, 2023

Related U.S. Application Data

(63) Continuation of application No. 17/929,496, filed on Sep. 2, 2022, now Pat. No. 11,717,655, which is a
(Continued)

(30) Foreign Application Priority Data

Dec. 6, 2007   (GB) ..................... 0723872

(51) Int. Cl.
*A61M 27/00* (2006.01)
*A61M 1/00* (2006.01)

(52) U.S. Cl.
CPC .............. *A61M 27/00* (2013.01); *A61M 1/85* (2021.05); *A61M 1/86* (2021.05); *A61M 1/90* (2021.05);
(Continued)

(58) Field of Classification Search
CPC .. A61M 1/0088; A61M 27/00; A61M 1/0031; A61M 1/0084; A61F 13/00068
See application file for complete search history.

(56) References Cited

U.S. PATENT DOCUMENTS

| 3,382,867 A | 5/1968 | Reaves |
| 3,568,675 A | 3/1971 | Harvey |

(Continued)

FOREIGN PATENT DOCUMENTS

| DE | 3935818 A1 | 5/1991 |
| DE | 19844355 A1 | 4/2000 |

(Continued)

OTHER PUBLICATIONS

Annex to the Communication for European Patent No. EP2231218, mailed on Apr. 17, 2019, 10 pages.
(Continued)

*Primary Examiner* — Guy K Townsend
(74) *Attorney, Agent, or Firm* — Knobbe, Martens, Olson & Bear, LLP

(57) ABSTRACT

Apparatus and a method for the provision of TNP therapy to a wound are described, the apparatus comprising: a sealing membrane (504) for covering a wound to form a wound cavity (500); one end of an aspirant conduit (522) operably associated with the wound cavity, vacuum means (524) provided at a distal end of the aspirant conduit for applying a vacuum to the wound cavity; and, air bleed means (510) in fluid communication with the wound cavity. Various embodiments of air bleed port members are also described.

20 Claims, 6 Drawing Sheets

Related U.S. Application Data continuation of application No. 16/791,985, filed on Feb. 14, 2020, now Pat. No. 11,433,176, which is a continuation of application No. 15/797,899, filed on Oct. 30, 2017, now Pat. No. 10,561,769, which is a continuation of application No. 14/267,721, filed on May 1, 2014, now Pat. No. 9,801,985, which is a continuation of application No. 12/746,458, filed as application No. PCT/GB2008/051118 on Nov. 26, 2008, now Pat. No. 8,734,410.

(52) U.S. Cl.
CPC .............. *A61M 1/915* (2021.05); *A61M 1/964* (2021.05); *A61M 1/962* (2021.05)

(56) References Cited

U.S. PATENT DOCUMENTS

| | | | |
|---|---|---|---|
| 3,633,567 | A | 1/1972 | Sarnoff |
| 3,902,484 | A | 9/1975 | Winters |
| 3,943,734 | A | 3/1976 | Fleissner |
| 4,135,515 | A | 1/1979 | Muriot |
| 4,306,558 | A | 12/1981 | Kurtz et al. |
| 4,487,606 | A | 12/1984 | Leviton et al. |
| 4,605,399 | A | 8/1986 | Weston et al. |
| 4,710,165 | A | 12/1987 | McNeil et al. |
| 4,822,743 | A | 4/1989 | Wegrzyn |
| 4,869,271 | A | 9/1989 | Idris |
| 4,903,710 | A | 2/1990 | Jessamine et al. |
| 4,921,492 | A | 5/1990 | Schultz et al. |
| 4,969,880 | A | 11/1990 | Zamierowski |
| 5,042,981 | A | 8/1991 | Gross |
| 5,056,510 | A | 10/1991 | Gilman |
| 5,088,483 | A | 2/1992 | Heinecke |
| 5,100,396 | A | 3/1992 | Zamierowski |
| 5,106,362 | A | 4/1992 | Gilman |
| 5,154,712 | A | 10/1992 | Herweck et al. |
| 5,160,315 | A | 11/1992 | Heinecke et al. |
| 5,180,375 | A | 1/1993 | Feibus |
| 5,183,763 | A | 2/1993 | Mallow et al. |
| 5,218,212 | A | 6/1993 | Sato et al. |
| 5,261,893 | A | 11/1993 | Zamierowski |
| 5,279,550 | A | 1/1994 | Habib et al. |
| 5,358,492 | A | 10/1994 | Feibus |
| 5,370,610 | A * | 12/1994 | Reynolds .............. A61M 27/00 604/43 |
| 5,383,476 | A | 1/1995 | Peimer et al. |
| 5,386,835 | A | 2/1995 | Elphick et al. |
| 5,449,347 | A | 9/1995 | Preen et al. |
| 5,466,229 | A | 11/1995 | Elson et al. |
| 5,520,652 | A | 5/1996 | Peterson |
| 5,527,293 | A | 6/1996 | Zamierowski |
| 5,531,855 | A | 7/1996 | Heinecke et al. |
| 5,599,289 | A | 2/1997 | Castellana |
| 5,599,333 | A * | 2/1997 | Atkinson .............. A61M 1/7411 604/326 |
| 5,618,556 | A | 4/1997 | Johns et al. |
| 5,636,643 | A | 6/1997 | Argenta et al. |
| 5,645,081 | A | 7/1997 | Argenta et al. |
| 5,678,564 | A | 10/1997 | Lawrence et al. |
| 5,701,917 | A | 12/1997 | Khouri |
| 5,704,905 | A | 1/1998 | Jensen et al. |
| 5,735,833 | A * | 4/1998 | Olson .................. A61M 35/00 604/289 |
| 5,738,656 | A | 4/1998 | Wagner |
| 5,753,285 | A | 5/1998 | Horan |
| 5,795,584 | A | 8/1998 | Totakura et al. |
| 5,816,252 | A | 10/1998 | Faries et al. |
| 5,885,237 | A | 3/1999 | Kadash et al. |
| 5,979,226 | A | 11/1999 | Cavestri et al. |
| 6,070,454 | A | 6/2000 | Cavestri |
| 6,070,455 | A | 6/2000 | Cavestri |
| 6,071,267 | A | 6/2000 | Zamierowski |
| D430,674 | S | 9/2000 | Dunshee et al. |
| 6,117,111 | A | 9/2000 | Fleischmann |
| 6,142,982 | A | 11/2000 | Hunt et al. |
| 6,149,614 | A | 11/2000 | Dunshee et al. |
| 6,345,623 | B1 * | 2/2002 | Heaton .................. A61M 1/912 602/42 |
| 6,458,109 | B1 | 10/2002 | Henley et al. |
| 6,500,112 | B1 | 12/2002 | Khouri |
| 6,553,998 | B2 * | 4/2003 | Heaton .................. A61M 1/912 602/42 |
| 6,626,891 | B2 | 9/2003 | Ohmstede |
| 6,648,862 | B2 * | 11/2003 | Watson .................. A61M 1/60 604/327 |
| 6,685,681 | B2 | 2/2004 | Lockwood et al. |
| 6,695,823 | B1 * | 2/2004 | Lina ........................ A61M 1/72 604/304 |
| 6,752,794 | B2 | 6/2004 | Lockwood et al. |
| 6,755,807 | B2 | 6/2004 | Risk, Jr. et al. |
| 6,764,462 | B2 | 7/2004 | Risk, Jr. et al. |
| 6,800,074 | B2 | 10/2004 | Henley et al. |
| 6,855,135 | B2 | 2/2005 | Lockwood et al. |
| 6,936,037 | B2 | 8/2005 | Bubb et al. |
| 6,942,687 | B1 | 9/2005 | Heaton et al. |
| 6,951,553 | B2 | 10/2005 | Bubb et al. |
| 6,960,190 | B2 | 11/2005 | Stinson |
| D515,701 | S | 2/2006 | Horhota et al. |
| 7,004,915 | B2 | 2/2006 | Boynton et al. |
| 7,022,113 | B2 | 4/2006 | Lockwood et al. |
| 7,070,584 | B2 | 7/2006 | Johnson et al. |
| 7,108,683 | B2 | 9/2006 | Zamierowski |
| 7,128,735 | B2 * | 10/2006 | Weston .................. A61M 27/00 604/313 |
| 7,195,624 | B2 * | 3/2007 | Lockwood ............. A61M 1/90 604/315 |
| 7,279,612 | B1 * | 10/2007 | Heaton .................. A61M 1/918 604/289 |
| 7,338,482 | B2 | 3/2008 | Lockwood et al. |
| 7,381,859 | B2 | 6/2008 | Hunt et al. |
| 7,438,705 | B2 * | 10/2008 | Karpowicz ............. A61M 1/86 604/327 |
| 7,485,112 | B2 | 2/2009 | Karpowicz et al. |
| 7,503,910 | B2 | 3/2009 | Adahan |
| 7,524,315 | B2 | 4/2009 | Blott et al. |
| 7,531,711 | B2 | 5/2009 | Sigurjonsson et al. |
| 7,534,927 | B2 | 5/2009 | Lockwood et al. |
| 7,553,306 | B1 | 6/2009 | Hunt et al. |
| 7,569,742 | B2 | 8/2009 | Haggstrom et al. |
| 7,608,066 | B2 | 10/2009 | Vogel |
| 7,625,362 | B2 | 12/2009 | Boehringer et al. |
| 7,645,269 | B2 | 1/2010 | Zamierowski |
| 7,651,484 | B2 | 1/2010 | Heaton et al. |
| 7,678,102 | B1 | 3/2010 | Heaton |
| 7,686,785 | B2 | 3/2010 | Boehringer et al. |
| 7,699,830 | B2 | 4/2010 | Martin |
| 7,699,831 | B2 | 4/2010 | Bengtson et al. |
| 7,700,819 | B2 | 4/2010 | Ambrosio et al. |
| 7,708,724 | B2 | 5/2010 | Weston |
| 7,709,694 | B2 | 5/2010 | Batich et al. |
| 7,722,582 | B2 | 5/2010 | Lina et al. |
| 7,753,894 | B2 | 7/2010 | Blott et al. |
| 7,776,028 | B2 | 8/2010 | Miller et al. |
| 7,794,450 | B2 | 9/2010 | Blott et al. |
| 7,858,679 | B2 | 12/2010 | Messersmith et al. |
| 7,862,718 | B2 | 1/2011 | Doyen et al. |
| 7,880,050 | B2 | 2/2011 | Robinson et al. |
| 7,883,494 | B2 | 2/2011 | Martin |
| 7,896,864 | B2 | 3/2011 | Lockwood et al. |
| 7,909,805 | B2 | 3/2011 | Weston |
| 7,922,703 | B2 | 4/2011 | Riesinger |
| 7,942,866 | B2 | 5/2011 | Radl et al. |
| 7,943,380 | B2 | 5/2011 | Westman et al. |
| 7,951,124 | B2 | 5/2011 | Boehringer et al. |
| 7,964,766 | B2 | 6/2011 | Blott et al. |
| 7,976,519 | B2 | 7/2011 | Bubb et al. |
| 7,994,383 | B2 | 8/2011 | Zocher |
| 7,999,145 | B2 * | 8/2011 | Kairinos .................. A61F 13/05 602/42 |
| 8,002,313 | B2 | 8/2011 | Singh et al. |
| 8,021,347 | B2 | 9/2011 | Vitaris et al. |

(56) References Cited

U.S. PATENT DOCUMENTS

| | | | |
|---|---|---|---|
| 8,057,449 B2 * | 11/2011 | Sanders | A61M 1/915 |
| | | | 604/319 |
| 8,062,272 B2 | 11/2011 | Weston | |
| 8,083,712 B2 | 12/2011 | Biggie et al. | |
| 8,092,441 B2 | 1/2012 | Sugito | |
| 8,105,295 B2 | 1/2012 | Blott et al. | |
| 8,118,794 B2 * | 2/2012 | Weston | A61F 13/00059 |
| | | | 604/315 |
| 8,129,580 B2 | 3/2012 | Wilkes et al. | |
| 8,133,211 B2 | 3/2012 | Cavanaugh, II et al. | |
| 8,147,468 B2 | 4/2012 | Barta et al. | |
| 8,152,785 B2 | 4/2012 | Vitaris | |
| 8,157,775 B2 | 4/2012 | Bobroff et al. | |
| 8,158,844 B2 | 4/2012 | McNeil | |
| 8,162,907 B2 | 4/2012 | Heagle | |
| 8,168,848 B2 | 5/2012 | Lockwood et al. | |
| 8,187,237 B2 | 5/2012 | Seegert | |
| 8,188,331 B2 | 5/2012 | Barta et al. | |
| 8,202,261 B2 | 6/2012 | Kazala, Jr. et al. | |
| 8,235,955 B2 | 8/2012 | Blott et al. | |
| 8,241,261 B2 | 8/2012 | Randolph et al. | |
| 8,246,606 B2 | 8/2012 | Stevenson et al. | |
| 8,246,607 B2 * | 8/2012 | Karpowicz | A61M 27/00 |
| | | | 604/313 |
| 8,257,327 B2 | 9/2012 | Blott et al. | |
| 8,267,908 B2 | 9/2012 | Coulthard | |
| 8,298,200 B2 * | 10/2012 | Vess | A61M 1/912 |
| | | | 604/313 |
| 8,317,774 B2 | 11/2012 | Adahan | |
| 8,348,910 B2 | 1/2013 | Blott et al. | |
| 8,366,692 B2 | 2/2013 | Weston et al. | |
| 8,376,972 B2 | 2/2013 | Fleischmann | |
| 8,382,731 B2 | 2/2013 | Johannison | |
| 8,399,730 B2 | 3/2013 | Kazala, Jr. et al. | |
| 8,409,170 B2 | 4/2013 | Locke et al. | |
| 8,430,867 B2 * | 4/2013 | Robinson | A61M 1/966 |
| | | | 604/313 |
| 8,449,508 B2 | 5/2013 | Coulthard et al. | |
| 8,460,255 B2 | 6/2013 | Joshi et al. | |
| 8,506,554 B2 | 8/2013 | Adahan | |
| 8,513,481 B2 | 8/2013 | Gergely et al. | |
| 8,545,466 B2 | 10/2013 | Andresen et al. | |
| 8,641,691 B2 | 2/2014 | Fink et al. | |
| 8,734,410 B2 * | 5/2014 | Hall | A61M 1/915 |
| | | | 604/319 |
| 8,734,419 B2 * | 5/2014 | Ormsby | A61F 13/5622 |
| | | | 604/385.15 |
| 8,764,732 B2 * | 7/2014 | Hartwell | A61M 1/912 |
| | | | 604/319 |
| 8,771,259 B2 * | 7/2014 | Karpowicz | A61M 1/96 |
| | | | 604/313 |
| 8,784,392 B2 * | 7/2014 | Vess | A61M 1/98 |
| | | | 604/304 |
| 8,784,393 B2 | 7/2014 | Weston et al. | |
| 8,795,243 B2 | 8/2014 | Weston | |
| 8,801,685 B2 | 8/2014 | Armstrong et al. | |
| 8,808,274 B2 | 8/2014 | Hartwell | |
| 8,843,327 B2 | 9/2014 | Vernon-Harcourt et al. | |
| 8,915,896 B2 * | 12/2014 | Sanders | A61M 1/982 |
| | | | 604/319 |
| 9,033,942 B2 | 5/2015 | Vess | |
| 9,044,579 B2 | 6/2015 | Blott et al. | |
| 9,199,012 B2 | 12/2015 | Vitaris et al. | |
| 9,302,032 B2 | 4/2016 | Bannister et al. | |
| 9,452,245 B2 | 9/2016 | Jaeb et al. | |
| 9,474,654 B2 | 10/2016 | Heagle et al. | |
| 9,539,373 B2 | 1/2017 | Jones et al. | |
| 9,585,990 B2 * | 3/2017 | Karpowicz | A61M 1/74 |
| 9,801,985 B2 * | 10/2017 | Hall | A61M 27/00 |
| 9,907,703 B2 | 3/2018 | Allen et al. | |
| 9,956,121 B2 * | 5/2018 | Hartwell | A61M 1/985 |
| 10,016,309 B2 * | 7/2018 | Hartwell | A61F 13/022 |
| 10,123,909 B2 * | 11/2018 | Hartwell | A61F 13/05 |
| 10,231,875 B2 * | 3/2019 | Hartwell | A61M 1/915 |
| 10,555,839 B2 * | 2/2020 | Hartwell | A61M 1/962 |
| 10,561,769 B2 * | 2/2020 | Hall | A61M 1/85 |
| 10,610,414 B2 * | 4/2020 | Hartwell | A61F 13/05 |
| 10,744,041 B2 * | 8/2020 | Hartwell | A61F 13/0226 |
| 11,129,751 B2 * | 9/2021 | Hartwell | A61F 13/0226 |
| 11,179,276 B2 * | 11/2021 | Hartwell | A61M 1/90 |
| 11,351,064 B2 * | 6/2022 | Hartwell | A61F 13/0253 |
| 11,364,151 B2 * | 6/2022 | Hartwell | A61F 13/00063 |
| 11,433,176 B2 * | 9/2022 | Hall | A61M 1/86 |
| 11,596,552 B2 * | 3/2023 | Hartwell | A61F 13/05 |
| 11,717,655 B2 * | 8/2023 | Hall | A61M 1/86 |
| | | | 604/319 |
| 2002/0044891 A1 | 4/2002 | Miller et al. | |
| 2003/0040687 A1 * | 2/2003 | Boynton | A61M 1/784 |
| | | | 601/6 |
| 2003/0069529 A1 | 4/2003 | Augustine et al. | |
| 2003/0097100 A1 * | 5/2003 | Watson | A61M 1/60 |
| | | | 604/323 |
| 2003/0212357 A1 * | 11/2003 | Pace | A61M 1/85 |
| | | | 602/41 |
| 2004/0006319 A1 * | 1/2004 | Lina | A61M 1/962 |
| | | | 604/304 |
| 2004/0200480 A1 | 10/2004 | Faries et al. | |
| 2004/0200483 A1 | 10/2004 | Faries et al. | |
| 2004/0208780 A1 | 10/2004 | Faries et al. | |
| 2004/0258562 A1 | 12/2004 | Mills et al. | |
| 2005/0004234 A1 | 1/2005 | Bell et al. | |
| 2005/0004534 A1 * | 1/2005 | Lockwood | A61M 39/223 |
| | | | 604/304 |
| 2005/0112772 A1 | 5/2005 | Farone et al. | |
| 2005/0137539 A1 | 6/2005 | Biggie et al. | |
| 2006/0155260 A1 * | 7/2006 | Blott | A61M 1/916 |
| | | | 604/317 |
| 2006/0194324 A1 | 8/2006 | Faries, Jr. et al. | |
| 2007/0005028 A1 | 1/2007 | Risk, Jr. et al. | |
| 2007/0016152 A1 * | 1/2007 | Karpowicz | A61M 1/80 |
| | | | 604/326 |
| 2007/0027423 A1 | 2/2007 | Scheinberg et al. | |
| 2007/0078444 A1 | 4/2007 | Larsson | |
| 2007/0089753 A1 | 4/2007 | Faries, Jr. et al. | |
| 2007/0167926 A1 * | 7/2007 | Blott | A61M 3/0229 |
| | | | 604/304 |
| 2007/0219532 A1 * | 9/2007 | Karpowicz | A61M 1/96 |
| | | | 604/540 |
| 2007/0225663 A1 | 9/2007 | Watt et al. | |
| 2007/0260226 A1 | 11/2007 | Jaeb et al. | |
| 2007/0265586 A1 | 11/2007 | Joshi et al. | |
| 2008/0033325 A1 | 2/2008 | Van Der Hulst | |
| 2008/0071214 A1 | 3/2008 | Locke et al. | |
| 2008/0071216 A1 | 3/2008 | Locke et al. | |
| 2008/0148817 A1 | 6/2008 | Miller et al. | |
| 2009/0005744 A1 * | 1/2009 | Karpowicz | A61M 1/72 |
| | | | 604/326 |
| 2009/0030383 A1 | 1/2009 | Larsen et al. | |
| 2009/0054855 A1 | 2/2009 | Blott et al. | |
| 2009/0131892 A1 | 5/2009 | Karpowicz et al. | |
| 2009/0137973 A1 * | 5/2009 | Karpowicz | A61M 1/86 |
| | | | 604/313 |
| 2009/0157016 A1 | 6/2009 | Adahan | |
| 2009/0192467 A1 | 7/2009 | Hansen et al. | |
| 2009/0221977 A1 | 9/2009 | Blott et al. | |
| 2009/0234309 A1 * | 9/2009 | Vitaris | A61M 1/915 |
| | | | 602/57 |
| 2009/0238811 A1 | 9/2009 | McDaniel et al. | |
| 2009/0254053 A1 | 10/2009 | Svensby et al. | |
| 2009/0254066 A1 | 10/2009 | Heaton et al. | |
| 2009/0293887 A1 | 12/2009 | Wilkes et al. | |
| 2009/0299257 A1 | 12/2009 | Long et al. | |
| 2009/0299308 A1 | 12/2009 | Kazala, Jr. et al. | |
| 2009/0299340 A1 | 12/2009 | Kazala, Jr. et al. | |
| 2009/0301382 A1 | 12/2009 | Patel | |
| 2009/0312723 A1 * | 12/2009 | Blott | A61M 3/0216 |
| | | | 604/290 |
| 2010/0030167 A1 | 2/2010 | Thirstrup et al. | |
| 2010/0069850 A1 | 3/2010 | Fabo | |
| 2010/0069863 A1 | 3/2010 | Olson | |
| 2010/0069886 A1 | 3/2010 | Wilkes | |
| 2010/0094234 A1 | 4/2010 | Ramella et al. | |

(56) References Cited

U.S. PATENT DOCUMENTS

| | | | |
|---|---|---|---|
| 2010/0106114 A1* | 4/2010 | Weston | A61M 25/02 602/54 |
| 2010/0106188 A1 | 4/2010 | Heaton et al. | |
| 2010/0125258 A1 | 5/2010 | Coulthard et al. | |
| 2010/0125259 A1 | 5/2010 | Olson | |
| 2010/0160901 A1 | 6/2010 | Hu et al. | |
| 2010/0211030 A1 | 8/2010 | Turner et al. | |
| 2010/0233146 A1 | 9/2010 | McDaniel | |
| 2010/0234818 A1 | 9/2010 | Aali | |
| 2010/0249733 A9 | 9/2010 | Blott et al. | |
| 2010/0262095 A1* | 10/2010 | Hall | A61M 1/915 604/319 |
| 2011/0028918 A1* | 2/2011 | Hartwell | A61F 13/0226 604/319 |
| 2011/0034888 A1 | 2/2011 | Aali | |
| 2011/0112492 A1* | 5/2011 | Bharti | A61F 13/05 604/319 |
| 2011/0118683 A1* | 5/2011 | Weston | A61M 1/732 604/319 |
| 2011/0130712 A1 | 6/2011 | Topaz | |
| 2011/0250626 A1 | 10/2011 | Williams et al. | |
| 2011/0251569 A1 | 10/2011 | Turner et al. | |
| 2012/0130332 A1 | 5/2012 | Cotton et al. | |
| 2012/0143156 A1* | 6/2012 | Bannister | A61M 39/0247 604/319 |
| 2012/0289915 A1* | 11/2012 | Karpowicz | A61M 1/86 604/319 |
| 2013/0226152 A1* | 8/2013 | Zolli | A61F 9/00745 604/540 |
| 2014/0228791 A1* | 8/2014 | Hartwell | A61F 13/00063 604/319 |
| 2014/0330225 A1* | 11/2014 | Hall | A61M 1/915 604/319 |
| 2014/0336602 A1* | 11/2014 | Karpowicz | A61M 1/74 604/319 |
| 2014/0350494 A1* | 11/2014 | Hartwell | A61F 13/022 604/319 |
| 2015/0141941 A1* | 5/2015 | Allen | A61F 13/022 604/319 |
| 2016/0081859 A1* | 3/2016 | Hartwell | A61M 1/962 604/319 |
| 2017/0143552 A1* | 5/2017 | Hartwell | A61F 13/01029 |
| 2017/0181896 A1* | 6/2017 | Hartwell | A61F 13/00063 |
| 2017/0181897 A1* | 6/2017 | Hartwell | A61F 13/0253 |
| 2017/0266051 A1* | 9/2017 | Hartwell | A61F 13/0209 |
| 2018/0133065 A1* | 5/2018 | Hartwell | A61M 1/962 |
| 2018/0235816 A1* | 8/2018 | Hartwell | A61F 13/0206 |
| 2018/0243142 A1* | 8/2018 | Hartwell | A61M 1/962 |
| 2018/0311078 A1* | 11/2018 | Hartwell | A61F 13/0253 |
| 2020/0100945 A1 | 4/2020 | Albert et al. | |
| 2020/0297541 A1* | 9/2020 | Hartwell | A61F 13/022 |
| 2022/0226160 A1* | 7/2022 | Hartwell | A61M 1/90 |
| 2023/0018964 A1 | 1/2023 | Joshi et al. | |
| 2023/0026081 A1* | 1/2023 | Hartwell | A61M 1/90 |

FOREIGN PATENT DOCUMENTS

| | | |
|---|---|---|
| EP | 0853950 A1 | 7/1998 |
| EP | 0777504 B1 | 10/1998 |
| EP | 0690706 B1 | 11/2000 |
| EP | 0921775 B1 | 12/2001 |
| EP | 1169071 A1 | 1/2002 |
| EP | 0853950 B1 | 10/2002 |
| EP | 0708620 B1 | 5/2003 |
| EP | 1448261 A1 | 8/2004 |
| EP | 0982015 B1 | 8/2006 |
| EP | 1772160 B1 | 6/2009 |
| EP | 1513478 B1 | 12/2009 |
| EP | 1637088 B1 | 1/2010 |
| EP | 2127690 A3 | 3/2010 |
| EP | 2319550 A1 | 5/2011 |
| EP | 1578477 B1 | 9/2011 |
| EP | 2545946 A3 | 3/2013 |
| EP | 2659915 A1 | 11/2013 |
| FR | 1163907 A | 10/1958 |
| GB | 2336546 B | 6/2000 |
| JP | S6180018 U | 5/1986 |
| JP | 2005334188 A | 12/2005 |
| WO | WO-9718007 A1 | 5/1997 |
| WO | WO-9901173 A1 | 1/1999 |
| WO | WO-0021586 A1 | 4/2000 |
| WO | WO-03030966 A1 | 4/2003 |
| WO | WO-03045492 A1 | 6/2003 |
| WO | WO-03057070 A2 | 7/2003 |
| WO | WO-03086232 A2 | 10/2003 |
| WO | WO-03092620 A2 | 11/2003 |
| WO | WO-03101508 A2 | 12/2003 |
| WO | WO-2004037334 A1 | 5/2004 |
| WO | WO-2004060148 A2 | 7/2004 |
| WO | WO-2005004670 A2 | 1/2005 |
| WO | WO-2005016179 A2 | 2/2005 |
| WO | WO-2005061025 A1 | 7/2005 |
| WO | WO-2005105174 A1 | 11/2005 |
| WO | WO-2005105180 A1 | 11/2005 |
| WO | WO-2006052338 A2 | 5/2006 |
| WO | WO-2006052745 A2 | 5/2006 |
| WO | WO-2007006306 A2 | 1/2007 |
| WO | WO-2007013049 A1 | 2/2007 |
| WO | WO-2007013064 A1 | 2/2007 |
| WO | WO-2007016590 A2 | 2/2007 |
| WO | WO-2007019038 A2 | 2/2007 |
| WO | WO-2007041642 A2 | 4/2007 |
| WO | WO-2007067685 A2 | 6/2007 |
| WO | WO-2007085396 A1 | 8/2007 |
| WO | WO-2007087810 A2 | 8/2007 |
| WO | WO-2007092397 A2 | 8/2007 |
| WO | WO-2007095180 A2 | 8/2007 |
| WO | WO-2007106590 A2 | 9/2007 |
| WO | WO-2007106591 A2 | 9/2007 |
| WO | WO-2008008032 A1 | 1/2008 |
| WO | WO-2008010094 A2 | 1/2008 |
| WO | WO-2008012278 A1 | 1/2008 |
| WO | WO-2008027449 A2 | 3/2008 |
| WO | WO-2008030872 A1 | 3/2008 |
| WO | WO-2008036360 A2 | 3/2008 |
| WO | WO-2008039314 A2 | 4/2008 |
| WO | WO-2008043067 A1 | 4/2008 |
| WO | WO-2008048481 A2 | 4/2008 |
| WO | WO-2008100437 A1 | 8/2008 |
| WO | WO-2008100440 A1 | 8/2008 |
| WO | WO-2008100446 A2 | 8/2008 |
| WO | WO-2008131895 A1 | 11/2008 |
| WO | WO-2008135997 A2 | 11/2008 |
| WO | WO-2008141470 A1 | 11/2008 |
| WO | WO-2009002260 A1 | 12/2008 |
| WO | WO-2009019419 A1 | 2/2009 |
| WO | WO-2009019495 A1 | 2/2009 |
| WO | WO-2009066104 A1 | 5/2009 |
| WO | WO-2009068665 A1 | 6/2009 |
| WO | WO-2009071933 A2 | 6/2009 |
| WO | WO-2009086580 A1 | 7/2009 |
| WO | WO-2009088925 A1 | 7/2009 |
| WO | WO-2009089390 A2 | 7/2009 |
| WO | WO-2009111655 A2 | 9/2009 |
| WO | WO-2009126103 A1 | 10/2009 |
| WO | WO-2009137194 A2 | 11/2009 |
| WO | WO-2009140376 A1 | 11/2009 |
| WO | WO-2009141820 A1 | 11/2009 |
| WO | WO-2009145894 A1 | 12/2009 |
| WO | WO-2009158125 A1 | 12/2009 |
| WO | WO-2009158126 A1 | 12/2009 |
| WO | WO-2009158127 A1 | 12/2009 |
| WO | WO-2009158129 A1 | 12/2009 |
| WO | WO-2010014177 A1 | 2/2010 |
| WO | WO-2010033271 A1 | 3/2010 |
| WO | WO-2010033272 A1 | 3/2010 |
| WO | WO-2010033769 A1 | 3/2010 |
| WO | WO-2010042240 A1 | 4/2010 |
| WO | WO-2010051073 A1 | 5/2010 |
| WO | WO-2010059712 A2 | 5/2010 |
| WO | WO-2010059730 A2 | 5/2010 |

(56) References Cited

FOREIGN PATENT DOCUMENTS

OTHER PUBLICATIONS

Boehringer Wound Systems, LLC, "Engenex™," Instructions for Use, Aug. 2007, pp. 1-33.
Brief Communication—Letter from the Opponent, re the Opposition of European Patent No. EP2231218, dated Sep. 17, 2019, 5 pages.
Brief Communication—Letter from the Proprietor of the Patent, re the Opposition of European Patent No. EP 2231218, dated Sep. 17, 2019, 3 pages.
Brief Communication—Letter from the Proprietor of the Patent for European Patent No. EP2231218, mailed on Dec. 18, 2018, 24 pages.
Communication of a Notice of Opposition including Statement of Facts and Evidence for European Patent No. EP2231218, mailed on Jul. 2, 2018, 17 pages.
Communication of the Board of Appeal for European Patent No. 2231218, mailed Jul. 13, 2023, 6 pages.
Edlich R.F., et al., "Evaluation of a New, Improved Surgical Drainage System", The American Journal of Surgery, vol. 149(2), Feb. 1985, pp. 295-298.
Info V.A.C. User Manual, KCI on Dec. 1, 2006 in 76 pages.
International Preliminary Report on Patentability for Application No. PCT/GB2008/051118, mailed Jun. 8, 2010, 10 pages.
International Search Report for Application No. PCT/GB2008/051118, mailed on Jun. 19, 2009, 6 pages.
Notice of Appeal against the Interlocutory Decision of the Opposition Division for European Patent No. EP2231218B1, mailed on Feb. 20, 2020, 4 pages.
Notice of Appeal against the Decision of the Opposition Division for European Patent No. EP2231218B1, mailed on Mar. 2, 2020, 4 pages.
Notice of Opposition—Statement of Facts and Evidence for European Patent No. EP2231218, mailed on Jun. 21, 2018, 16 pages.
Opponent Appellant's Grounds of Appeal for European Patent No. 2231218, mailed May 1, 2020, 9 pages.
Reply of the Patent Proprietor to the Notice(s) of Opposition for European Patent No. EP2231218, mailed on Nov. 28, 2018, 26 pages.
Smith S.R.G., "Surgical Drainage," Surgical symposium, British Journal of Hospital Medicine, Jun. 1985, pp. 308-315.
The Opposition Division Opinions for European Patent No. EP2231218B1, mailed Jan. 3, 2020, 61 pages.
The Wayback Machine, "Comfort advantages with AirX™," Retrieved from the Internet: https://web.archive.org/web/20070714011844/http://www.air-x.net/content/view/2/3/lang/ , on Jul. 14, 2007, 1 page.
The Wayback Machine, "Moisture-Transporting Material," Retrieved from the Internet: https://web.archive.org/web/20070714011837/http://www.air-x.net/content/view/1/2/lang/ , on Jul. 14, 2007, 1 page.
Van Way, C.W., "Prevention of Suction-Induced Gastric Mucosal Damage in Dogs," Critical Care Medicine, vol. 15, No. 8, Aug. 1987, pp. 774-777.
Worth M.H., et al., "The Effectiveness of Bacterial Filtration in Vented Wound Drains," Journal of Surgical Research, vol. 27(6), Dec. 1979, pp. 405-407.
Letter relating to the Appeal Procedure for the Opposition of the European Patent No. 2231218, mailed on Aug. 8, 2023, 7 pages.
Minutes of the Oral Proceedings of Nov. 16, 2023 for European Patent No. 2231218, mailed on Nov. 28, 2023, 3 pages.
Notifications of the Decision of the Board of Appeal for European Patent No. 2231218, dated Dec. 22, 2023, 17 pages.

\* cited by examiner

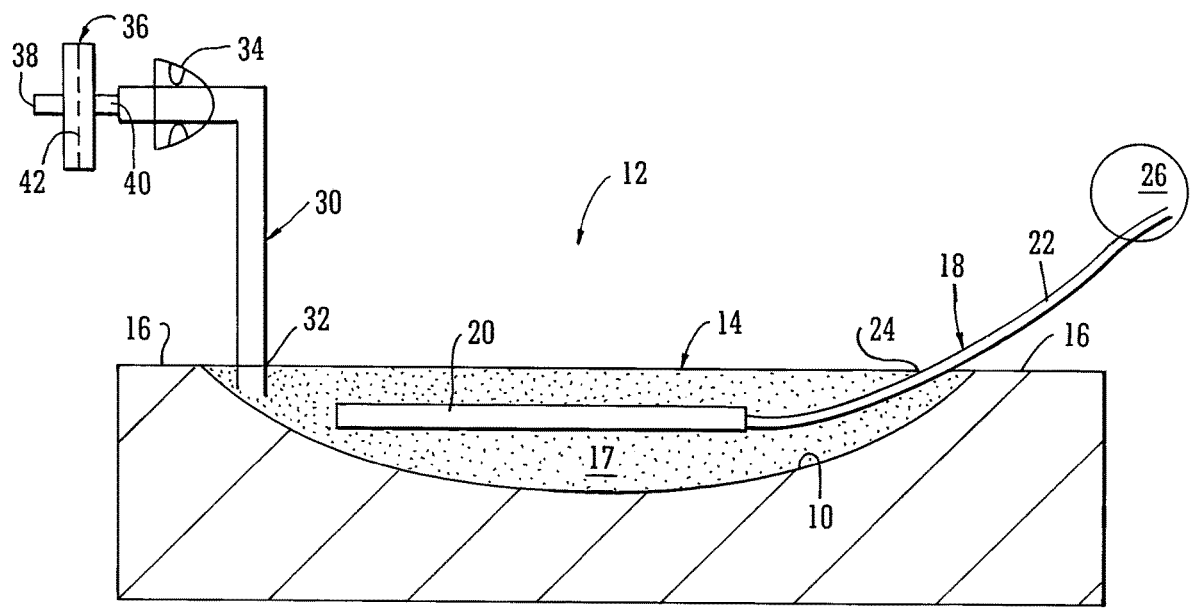
FIG. 1
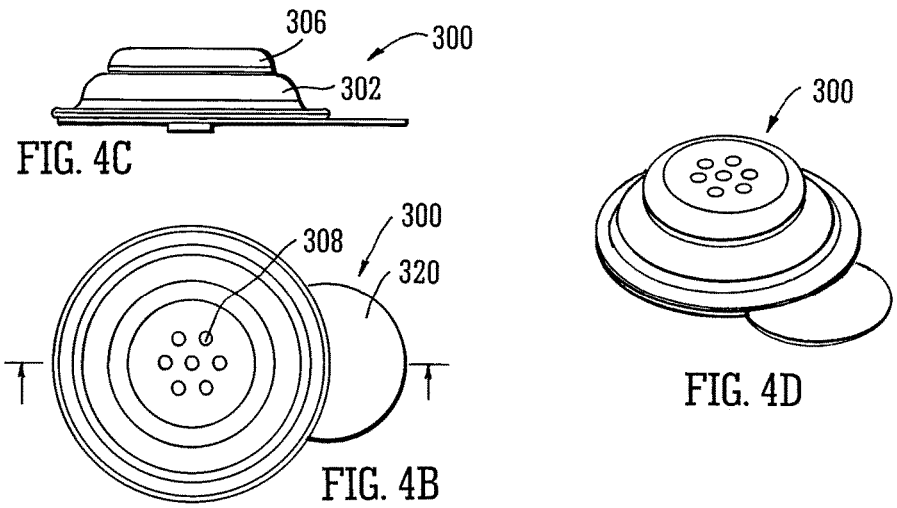
FIG. 4C
FIG. 4B
FIG. 4D
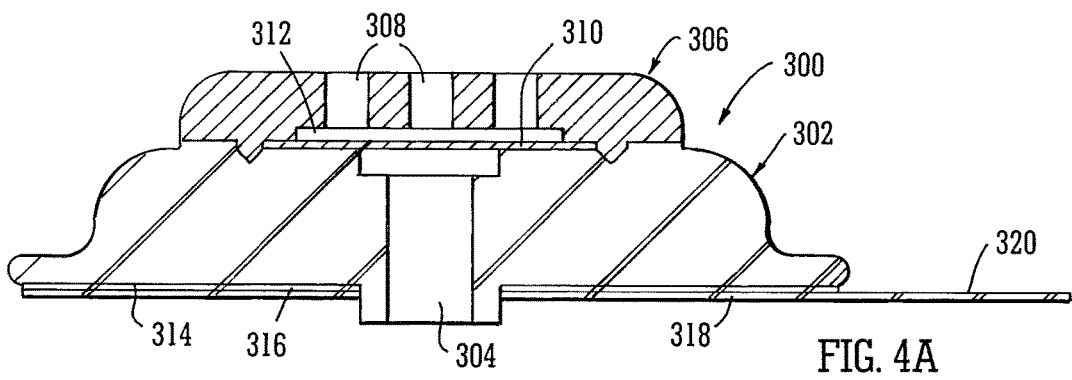
FIG. 4A

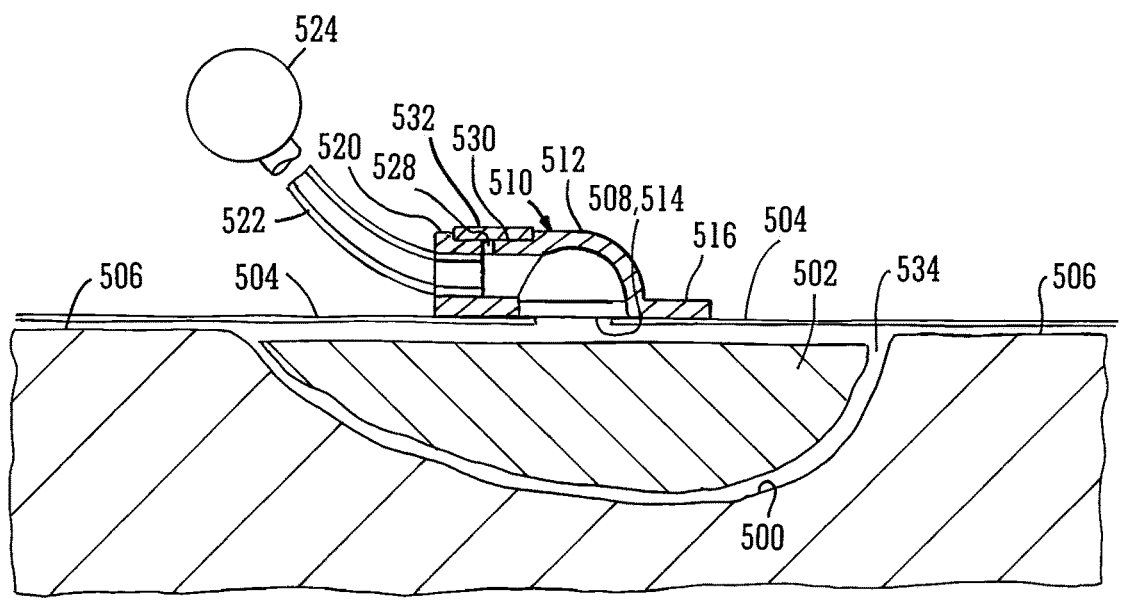
FIG. 5
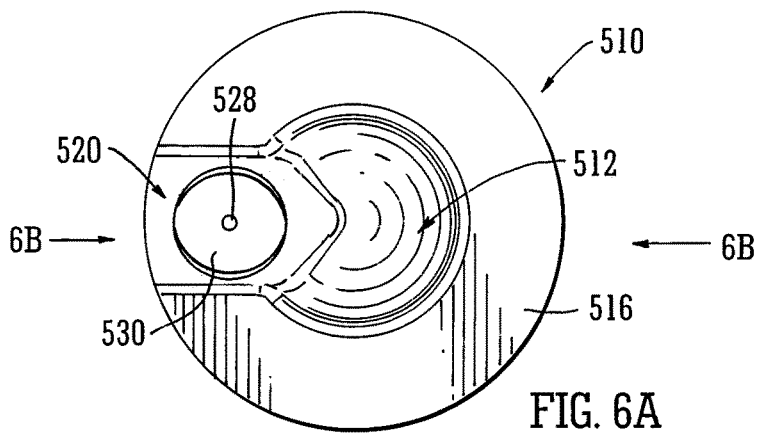
FIG. 6A
FIG. 6B
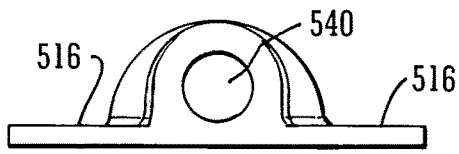
FIG. 6C
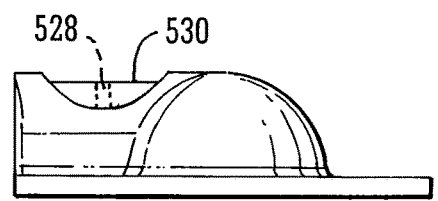
FIG. 6D

APPARATUS FOR TOPICAL NEGATIVE PRESSURE THERAPY

CROSS-REFERENCE TO RELATED APPLICATIONS

The present application is a continuation of U.S. patent application Ser. No. 17/929,496, filed Sep. 2, 20233, which is a continuation of U.S. patent application Ser. No. 16/791,985, filed Feb. 14, 2020 and now U.S. Pat. No. 11,433,176, which is a continuation of U.S. patent application Ser. No. 15/797,899, filed Oct. 30, 2017 and now U.S. Pat. No. 10,561,769, which is a continuation of U.S. patent application Ser. No. 14/267,721, filed May 1, 2014 and now U.S. Pat. No. 9,801,985, which is a continuation of U.S. patent application Ser. No. 12/746,458, filed on Jun. 4, 2010, entitled "APPARATUS FOR TOPICAL NEGATIVE PRESSURE THERAPY," which is a national phase application under 35 U.S.C. § 371 of International Application No. PCT/GB2008/051118, filed on Nov. 26, 2008, entitled "APPARATUS FOR TOPICAL NEGATIVE PRESSURE THERAPY," which claims the benefit of Great Britain Application No. 0723872.8, filed Dec. 6, 2007, entitled "APPARATUS FOR TOPICAL NEGATIVE PRESSURE THERAPY," the entire contents of each of which is hereby incorporated by reference herein in their entirety and for all purposes.

TECHNICAL FIELD

The present invention relates to topical negative pressure (TNP) therapy particularly, though not exclusively, to the control of negative pressure within a wound dressing.

SUMMARY

TNP therapy has assumed great importance in recent years due to the beneficial effects of TNP therapy on a healing wound and also because of the accelerated healing which TNP therapy provides.

Apparatus for TNP therapy ranges from extremely complex apparatus only really suitable for use in a specialised hospital environment to much smaller and simpler, portable apparatus which may be used by an individual patient at home or at work.

The basic principle of TNP therapy is to create a closed cavity over the wound itself by means of a thin, flexible sealing film adhered to the patient's sound skin surrounding the wound; admitting one end of an aspirant conduit into the closed cavity, the conduit being sealed to the flexible film, for example; and connecting a distal end of the aspirant conduit to a vacuum source such as an electrically driven vacuum pump, for example, to create a pressure lower than the surrounding ambient atmospheric pressure within the wound cavity. As is known to the skilled person the lower pressure creates many beneficial therapeutic effects on the wound including increased blood flow to the wound and faster granulation of tissue, for example.

As noted above TNP therapy may be applied by a diverse range of apparatus. However, in general terms the more complex apparatus tends to be used on larger, more serious wounds which require a more intensive and varied treatments by TNP therapy. Examples of apparatus useful in the context of treatment of such larger wounds are given below.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Whilst the above examples are mainly relevant to the treatment of larger wounds, there is also a need for the treatment of relatively small wounds where the patient may otherwise be fit and mobile and require treatment outside of a clinical setting such as at home or at their workplace but where the provision of TNP therapy is desirable but nevertheless need to provide controlled conditions in the wound cavity. An example of a suitable apparatus is described in our co-pending UK patent application, GB0712736.8, of common ownership herewith, the content of which is included herein by reference.

An unexpected problem with smaller wounds of relatively low surface area is that they are relatively easy to seal in that they generally may have a relatively large area of sound flesh surrounding them and hence have large sealing borders therearound for the sealing film or drape to seal with and which tends to mitigate against inward air leaks from this area of the dressing. Secondly, even though the sealing films, which are well known to those skilled in the art, tend to be semi-permeable membrane type materials which allow to an extent the passage of gas such as air and water vapour, they do so only to a limited extent which is defined or measured in mass flow per unit area. Thus, since the area of the sealing film above the wound is relatively small, the amount of permitted gaseous flow is small. Because the seal over and around the wound may be very good, it is easy to create a vacuum in the wound cavity which does not decay quickly due to leaks, and therefore, very little or no flow through the aspirant conduit may result and whilst the vacuum is there over the wound, the wound exudate may not be being transported away to a waste canister, for example, and may be stagnating at the wound itself, this being especially so at low levels of negative pressure relative to atmospheric pressure. One important feature of TNP therapy is that the wound exudate fluid is desirably transported away from the wound site. Failure to achieve this efficiently may result in increased risk of infection and in the worst cases may result in back flow of wound exudate into the wound cavity.

However, whether the wound is large or small the fact is that clinicians strive to seal the wound as well as they possibly can so as to prevent bacteria from causing infection. Larger wounds generate greater volumes of fluid and, are therefore, susceptible to filling the wound cavity with fluid. Furthermore, it is possible for the aspiration conduit to fill with exudate fluid resulting in a pressure differential between the wound and the vacuum source due to the viscous drag of the exudate and the height differential between wound and vacuum source.

It is an object of the present invention to mitigate such problems especially, but not exclusively, in portable TNP therapy apparatus and to provide apparatus and a method where reliable flow of wound exudate away from the wound is promoted.

According to a first aspect of the present invention there is provided apparatus for the provision of TNP therapy to a wound, the apparatus comprising: a sealing membrane for covering a wound to form a wound cavity in use; an aspirant conduit having one end thereof operably associated with the wound cavity, in use; vacuum means provided at a distal end of the aspirant conduit for applying a vacuum to the wound cavity when in use; and, air bleed means in fluid communication with the wound cavity when in use.

In this specification the term "vacuum" means a pressure less than ambient atmospheric pressure.

The air bleed means may be switchable in that the air bleed may be turned on and off as desired. In this regard the air bleed means may be provided by a second conduit having one end in communication with the wound cavity and having a filter associated with the conduit and a clamp or valve which enables the filter to admit air from the surrounding atmosphere to the wound cavity under the influence of the vacuum in the wound cavity. Air flow into the conduit may be controlled by the clamp on the conduit or on/off valve controlled by the user/patient or a clinician. An air bleed may be admitted when, for example, the patient observes that the aspirant tube appears to be full of exudate but which is not moving. Opening of the conduit to ambient air then induces a fluid flow in the conduit to expel the exudate into a waste canister, for example, associated with particular TNP apparatus in use.

The air bleed means may provide a maximum flow rate at 200 mmHg below atmospheric of up to 1 l/min into the system. Preferably, the flow rate may be a maximum of 0.5 l/min. More preferably the flow rate may be a maximum of 0.2 l/min. More preferably still, a maximum flow rate of 0.05 l/min may be provided into the system. The overriding factor is to achieve a flow rate consistent with the wound not drying out as may happen if the incoming flow rate of bleed air is too high.

Control of bleed rate may be achieved by control of the area of the filter through which bleed air may be admitted.

Use of a filter is both desirable and advantageous in minimising the risk of pathogens from being admitted to the wound cavity by the air bleed.

The use of a regulator on the second conduit described above may also be employed to achieve a constant but controlled rate of inward air bleed.

Alternatively, the air bleed means may be associated with the sealing drape in which an aperture may be formed to permit the attachment of an air bleed port thereto. Such an air bleed port may have a filter portion or aperture through which ambient air is drawn into the wound cavity by the vacuum. Such an air bleed port may be permanently open to ambient atmosphere but, due to the contained filter portion, may restrict the rate of flow of air into the wound cavity or aspirant conduit to a low rate due to the size of the filter pores. In effect such an air bleed port substitutes for leakage of air into a TNP dressing which normally occurs with larger wounds. Suitable air bleed ports may be manufactured from soft plastics material mouldings so as not to cause trauma to a patient if lain upon. They may be provided during manufacture with a layer of adhesive thereon and suitable protective layer of siliconised paper until needed for use.

Such air bleed ports may be sealed off with suitable sealing tape so as to be able to check for leaks in the dressing and/or act as an on/off facility.

An air bleed provision may be provided by a second conduit plugged into a suitable grommet sandwiched between two adhesive drape or sealing membrane layers for example as described in our co-pending International patent application, PCT/US2007/074374, based on GB0712735.0, of common ownership herewith and the content of which are included herein by reference.

Suitable filters may be 0.2 or 0.1 or 0.02 micron filters, for example, which also have the added advantage in that they may also prevent expulsion of bacteria to atmosphere in the reverse direction if for any reason this might occur.

An advantage of the present invention is that use of a filter element of predetermined pore size and area permits close control of a desired low flow rate of ambient air into the wound cavity, the filter element itself also preventing ingress of potentially harmful bacteria. In contrast, conventional valves are insufficiently sensitive to control at the low flow rates required and also do not stop harmful bacterial from entering the wound.

In some embodiments of the present invention an air bleed port such as that described above may be provided with the drape or sealing membrane material during manufacture thereof, the air bleed port being adhered or welded to the drape or flexible sealing membrane.

In all embodiments of the present invention the rate of bleed air flow into the dressing and wound cavity is controlled solely by the characteristics of the filter with respect to its pore size and area exposed to ambient atmosphere.

According to a second aspect of the present invention there is provided an air bleed port member for use with a topical negative pressure dressing.

According to a third aspect of the present invention there is provided a method of providing topical negative pressure therapy to a wound, the method comprising the steps of: providing a sealing membrane for covering a wound to form a wound cavity; providing an aspirant conduit having one end thereof operably associated with the wound cavity; providing vacuum means provided at a distal end of the aspirant conduit for applying a vacuum to the wound cavity; and, air bleed means in fluid communication with the wound cavity.

BRIEF DESCRIPTION OF THE DRAWINGS

In order that the present invention may be more fully understood, examples will now be described by way of illustration only with reference to the accompanying drawings, of which:

FIG. 1 shows a schematic cross section through a wound to which TNP therapy is being applied and also showing schematically one embodiment of the present invention;

FIGS. 4A to 4D which show various views of an embodiment of an air bleed port for attachment to a sealing membrane;

FIG. 5 shows a schematic cross section through a second wound having an alternative air bleed port member attached to the sealing membrane;

FIGS. 6A to 6D show various views and a cross section s of the air bleed port shown in FIG. 5;

DETAILED DESCRIPTION

Figure 2:
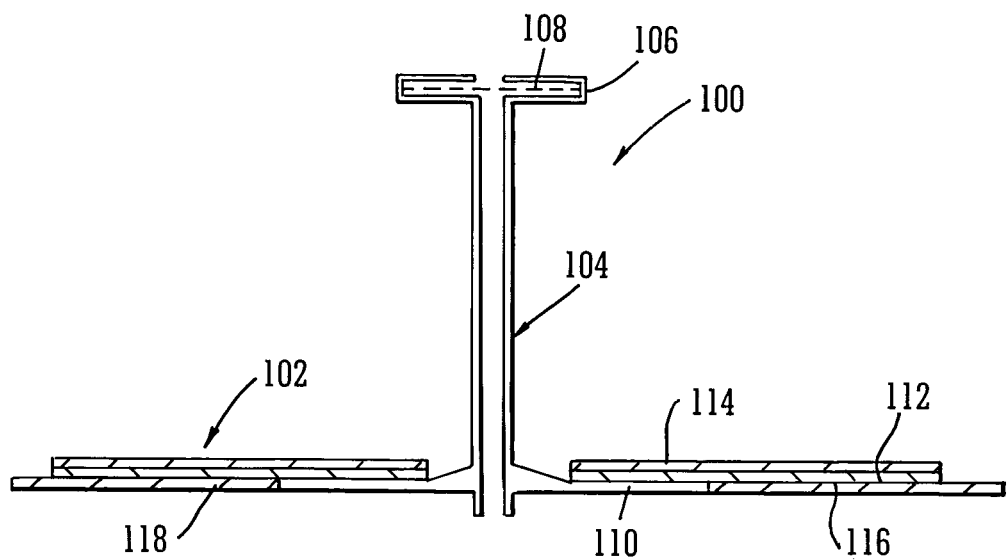
FIG. 2 shows across section through a schematic embodiment of a sealing membrane having an air bleed conduit and filter therewith.

Referring now to the drawings and where the same features are designated by common reference numerals.

FIG. 1 shows a schematic cross section through a wound 10 to which is applied apparatus 12 according to the present invention for administering TNP therapy to the wound. The wound 10 has a sealing membrane 14 covering it and sealed to sound flesh 16 around the border of the wound so as to define a wound cavity 17. An aspirant conduit 18 is provided, the conduit having a perforated drain portion 20 and a single lumen portion 22 attached thereto and which is sealed to the dressing at 24 where it passes through. The distal end of the conduit 18 is connected to a suitable vacuum pump 26. The dressing is provided with a second, short conduit portion 30 which accesses the wound cavity 17 through the membrane 14 and sealed thereto at 32. The conduit 30 is provided with a pinch clamp 34 which enables the soft plastics material of the conduit 30 to be either closed or open for flow. At the end of the conduit 30 is a small plastics material housing 36 having an air inlet 38 an air outlet 40 and in between a filter element 42. Thus, air entering the inlet 38 must flow through the filter element 42 in order to flow through the outlet 40 and through the conduit 30. Optionally, there may be a layer of porous, compression resistant wound filler (not shown) adjacent the wound surface 10 to prevent the sealing membrane 14 from being pulled down onto the wound surface by the applied vacuum and thereby preventing flow of wound exudate to the aspirant drain conduit portion 20 from the whole area of the wound. However, in FIG. 1 which is meant to represent a small area wound such a wound filler may not be necessary if the sealing membrane is sufficiently taught not to contact the wound surface under the applied vacuum.

In operation the vacuum pump is turned on and a vacuum is created in the wound cavity 17. If the wound cavity is well sealed with no or very little leakage, wound exudate fluid may not be transported along the conduit portion 22 to a waste receptacle (not shown) associated with the vacuum pump 26 since there is little or no air/fluid flow along the conduit 22. In this event the pinch clamp 34 may be opened so that an air bleed is admitted through the filter element 42 into the wound cavity 17 thus stimulating a fluid flow through the wound cavity 17 and through the conduit 22 towards the pump 26 so keeping the conduit 22 unblocked and free flowing. The pinch clamp 34 has no effect on the flow rate of the air bleed, merely controlling whether there is or is not flow through the conduit 30, all flow control being decided by the pore size and area of the filter element 42.

In this instance the filter 42 is a 0.2 micron pore size, antimicrobial filter

The pinch clamp may be left open so that the conduit 30 is permanently open in the event that the wound cavity is particularly well scaled so providing a constant air bleed whilst the vacuum pump 26 is running.

FIG. 2 shows a schematic cross section of a dressing 100 for use with the apparatus according to the present invention and comprises a sealing membrane portion 102 and a conduit portion 104 having a filter housing 106 and having a filter 108 therein. The dressing 100 may be manufactured as an entity, the conduit portion 104 being attached by an adhesive layer 112 to a membrane member 114 at a flange portion 110 associated with the conduit portion 104. The lower face 116 of the adhesive layer 112 is protected in known manner by a layer of protective siliconised paper 118. In this dressing portion the membrane 114 covers the wound being adhered to sound flesh at the border thereof by the adhesive layer 112. The conduit 104 may optionally be provided with a pinch clamp, for example, as in the embodiment shown in FIG. 1 and for the same purpose.

Figure 3:
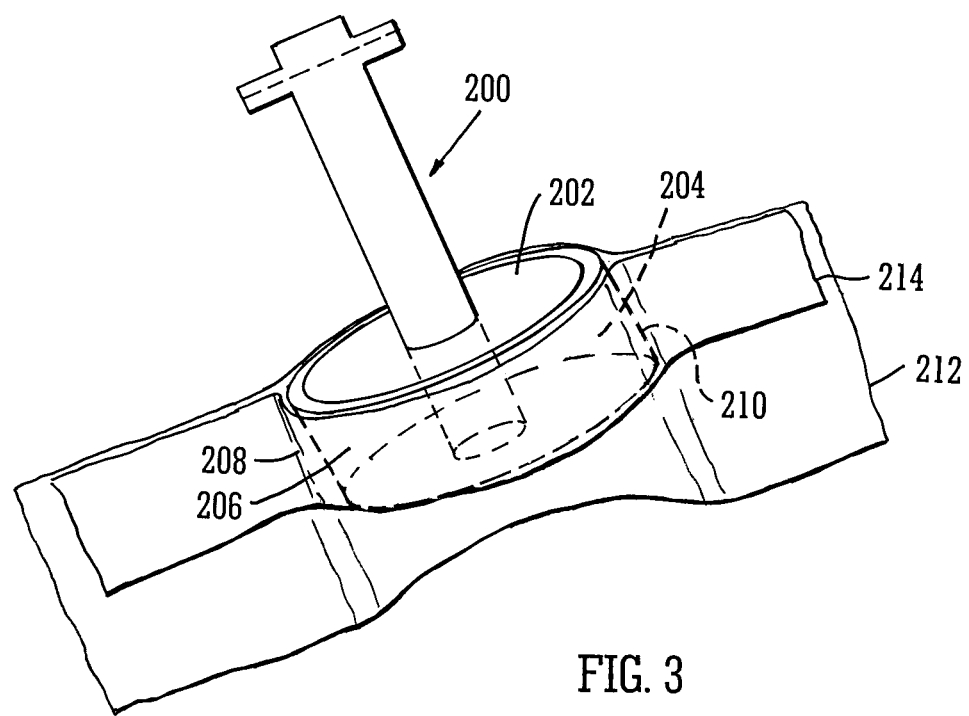
FIG. 3 shows a perspective view of a grommet for use in apparatus employing some embodiments of the present invention.
Figure 7A:
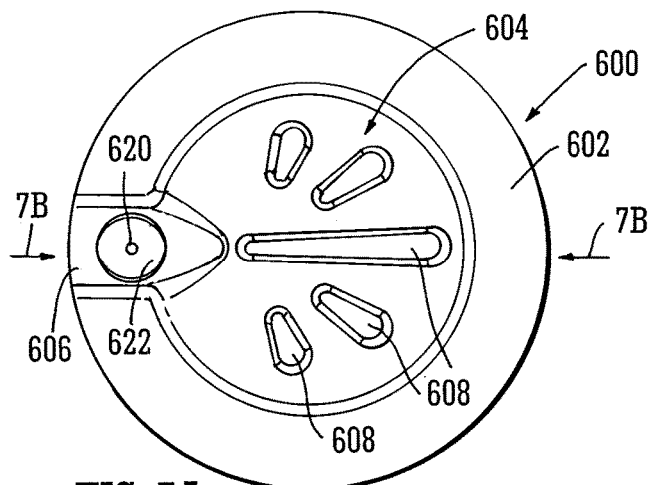
FIGS. 7A to 7F show various views and a cross section of a further alternative air bleed port for use with the dressing shown in FIG. 5.
Figure 7D:
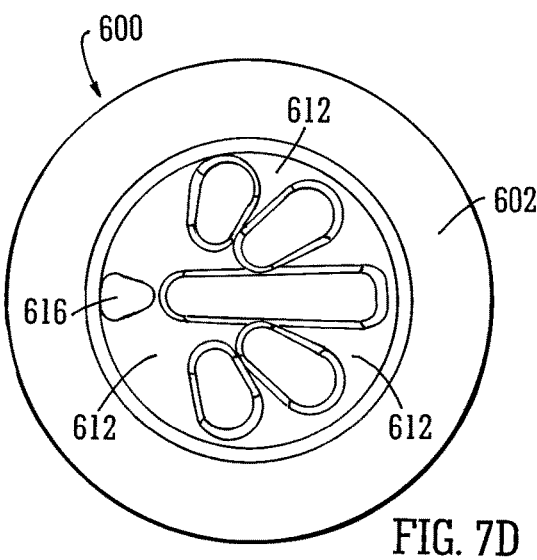
Figure 7B:
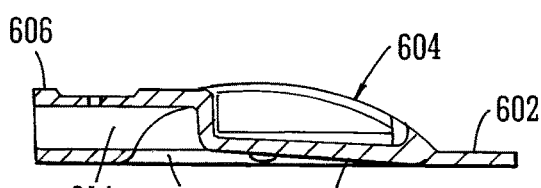
Figure 7E:
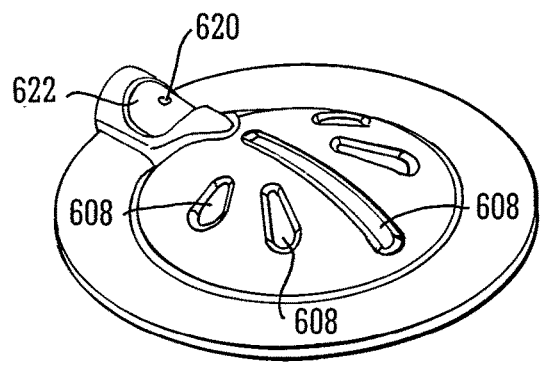
Figure 7C:
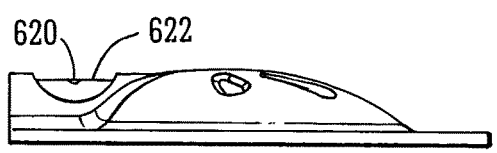
Figure 7F:
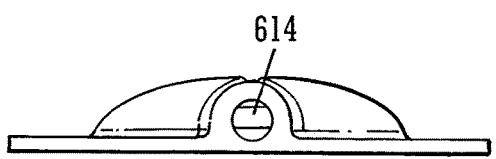
Figure 8A:
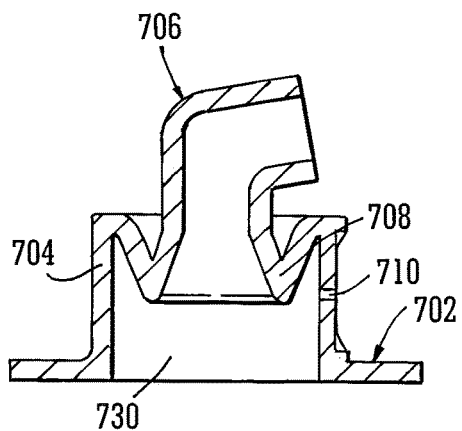
FIGS. 8A to 8E show various views and a cross section through an alternative air bleed port suitable for the dressing shown in FIG. 1.
Figure 8B:
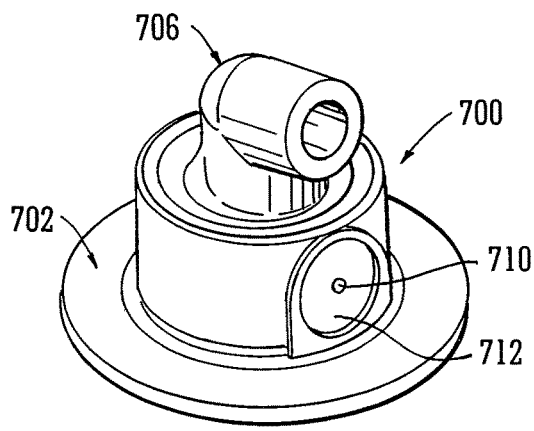
Figure 8C:
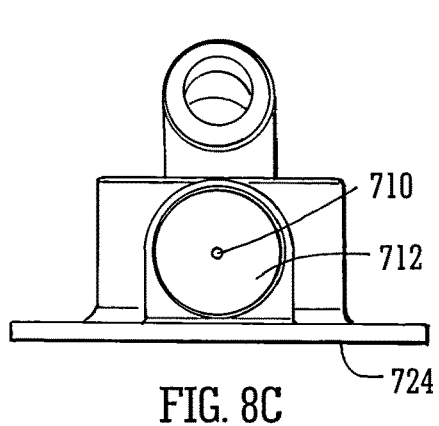
Figure 8D:
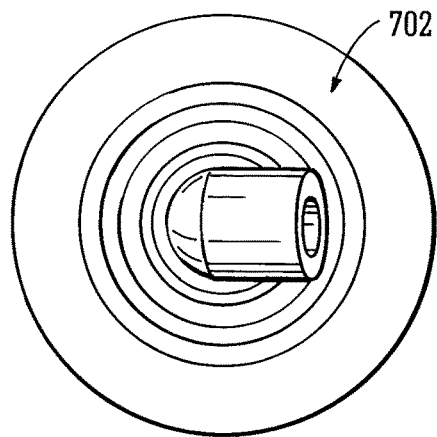
Figure 8E:
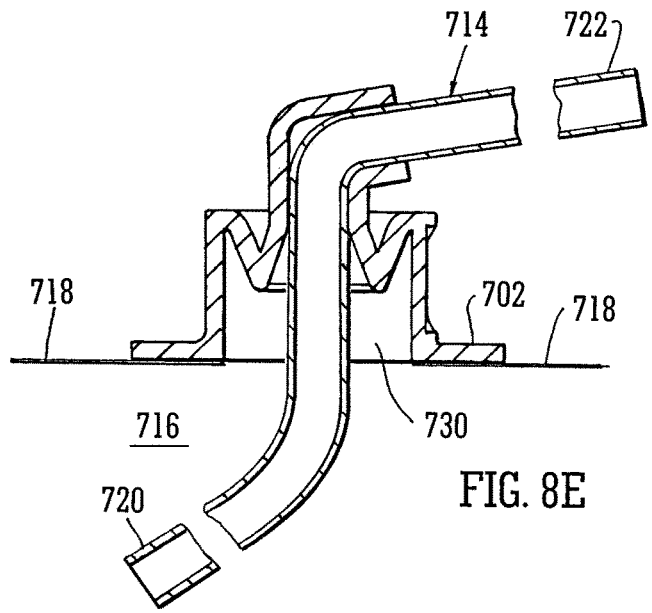

FIG. 3 shows a conduit 200 of the type shown in FIGS. 1 and 2 but plugged into a grommet member 202. The grommet member has two curved faces 204,206 which meet at tapered edges 208, 210. This assembly of conduit 200 and grommet is incorporated into a dressing by the grommet member being sandwiched between two layers 212, 214 of thin, flexible adhesively coated membrane material where adhesive coated faces of the membrane material (not shown) face each other and adhere to the faces 204, 206 as discussed in our co-pending International patent application, PCT/US2007/074374, mentioned above and of common ownership herewith. Other embodiments of grommets from PCT/US2007/074374 may also be utilised.

FIG. 4 shows various views of an air bleed port member 300 for attachment to a sealing membrane (not shown). FIG. 4A shows a cross section through the port member; FIG. 4B shows a plan view of the port member; FIG. 4C shows a view in elevation; and, FIG. 4D shows a perspective view of the port member 300. The port member 300 comprises a moulded body portion 302 having a centrally disposed aperture 304 therethrough; an upper cap portion 306 having air ports 308 therethrough; and, a filter element member 310 sandwiched between the body portion and the cap portion. The cap portion 306 also has a circular recess 312 in fluid communication with the air ports 308, the filter element 310 being exposed to the area of the recess 312. The bottom face 314 of the body portion has a layer of adhesive 316 thereon and which is protected prior to use with protective paper layer 318 which is removed before use by means of a protruding finger tab 320.

To use the air bleed port member, a hole (not shown) is made in the membrane (not shown) covering the wound commensurate with the size of the aperture 304, the protective paper layer 318 us removed and the air bleed port 300 adhered to the upper surface of the sealing membrane with the hole in the membrane and the aperture 304 in communication with each other.

In a preferred construction the air bleed port 300 may be provided as part of a dressing membrane with the port 300 and membrane adhered or welded (in the latter case there is no adhesive layer 316) together during manufacture.

FIG. 5 shows a wound 500 having therein a porous, resiliently compressible wound filling element 502 such as a polyurethane foam material, for example, cut to conform generally to the wound shape and size. The wound 500 is covered with a self-adhesive flexible sealing membrane 504 similar to that shown in FIG. 1 and which is adhered to sound flesh 506 surrounding the wound 500. The membrane 504 has an aperture 508 formed therein and over which is adhered an air bleed port 510. The port 510 has a domed shape 512 having an aperture 514 in a flanged base portion 516, the aperture 514 being made coincident with the aperture 508 in the membrane 504. The port 510 has a socket portion 520 to receive an aspirant conduit 522 which is connected to a vacuum pump 524 and an intervening waste canister (not shown). The socket portion 520 receives the end of the aspirant conduit 522 to an extent which leaves uncovered an air bleed hole 528 which has a surrounding recess 530 into which is adhered a filter element 532. The wound surface 500, membrane 504 and air bleed port 510 form between them a sealed cavity 534.

In operation the vacuum pump 524 generates a predetermined vacuum level in the cavity 534 which causes the membrane 504 to be pushed down onto the porous, resiliently compressible wound filling element 502 by the ambient excess air pressure and the apertures 508, 514 to come into direct contact with the top surface of the resiliently compressible foam material 502 thus aspirating wound exudate which permeates through the wound filling element 502 to the waste canister (not shown). Whilst the wound exudate is being aspirated, the air bleed hole 528 and filter 532 permit a continuous controlled rate air bleed into the conduit 522 preventing the aspiration of wound exudate from stagnating. If, for any reason, it is desired to stop the air bleed then this can be terminated by the simple expedient of placing a piece of non-porous adhesive tape over the hole and filter 532.

FIG. 6 shows the air bleed port 510 of FIG. 5. FIG. 6A shows a top plan view of the port.

FIG. 6B shows a cross section on the line 6B-6B of FIG. 6A; FIG. 6C shows a view looking in the direction of arrow 6B on the left of FIG. 6A; and FIG. 6D shows a side view in elevation. The air bleed port 510 is generally of domed circular form having a hollow domed portion 512 and a socket portion 520 having a passage 540 leading into the hollow portion 542. The port comprises a flat flange portion 516 having an adhesive layer 544 to adhere to a flexible sealing membrane and the adhesive layer being protected before use by a layer of siliconised paper (not shown) in known manner. The lower face of the flange portion 516 has an aperture 514 therein exposing the hollow portion 542. The socket portion receives an aspirant conduit, in use, as described with reference to FIG. 5 and also has an air bleed hole 528 lying in the centre of recessed portion 530 which receives a filter member as shown in FIG. 5. The pore size of the filter member and, to an extent the size of the hole 528 control the rate of air bleed into the aspirant conduit at the desired pressure in the wound cavity 534 (see FIG. 5). The port 510 may be moulded from a soft plastics material such as polyurethane or polypropylene, for example.

The port described with reference to FIG. 6 may be adhered to a sealing membrane as described above or adhered or welded thereto in a pre-prepared sealing membrane and port unit.

An important advantage of the port according to the embodiment of FIG. 6 is that it is particularly easy to apply to a wound in that the self adhesive membrane material merely needs adhering to sound flesh after first having placed a wound filling element in the wound, an aperture made in the membrane and the port adhered thereto (or a pre formed port/membrane applied to the wound and an aspirant conduit plugged into the socket portion 520. There is no need to seal the aspirant conduit to the sealing membrane and the number of steps for making a TNP therapy dressing is significantly reduced.

FIG. 7 shows an air bleed port 600 which may also be used with the dressing described with reference to FIG. 5. FIG. 7A shows a top plan view of the port; FIG. 7B shows a cross section on the line 7B-7B of FIG. 7A; FIG. 7C shows a side view in elevation of the port of FIG. 7A; FIG. 7D shows an underside plan view of the port of FIG. 7A; FIG. 7E shows a perspective view of the port; and, FIG. 7F shows a view of the port in the direction of arrow 7B on the left of FIG. 7A. The port 600 is of generally circular form having a flange portion 602, a shallow domed body portion 604 lying within the flange periphery and a socket portion 606. The shallow domed body portion 604 is not hollow but has a number of splayed unequal length finger-like indentations 608 formed in the upper surface thereof as an aid to stiffness. The indentations extend almost through the thickness of the domed portion save for a predetermined thickness of material 610 remaining on the underside. On the underside the spaces between the indentations create a space 612 in which vacuum may exist and wound exudate collect to be aspirated away by an associated aspirant conduit (not shown) connected to the socket portion 606 in the same manner as with the port of FIG. 6. The socket portion 606 has a passage 614 therethrough leading to an aperture 616 which connects with a co-operating aperture, in use, in a sealing membrane. The socket portion has an air bleed hole 620 and a recessed portion 622 to receive a filter element (not shown) in the same manner as the port of FIG. 6. As with FIG. 6, the aspirant conduit is only inserted into the passage 614 up to the air bleed hole 620 so as not to block it.

This port also adheres to the sealing membrane surface or may be pre-prepared by adhering or welding the port thereto as a unit. Where the port member 600 has a layer of adhesive on the underside of flange portion 602 it may be provided with a protector layer of siliconised paper or PE film (not shown) to be removed by the user immediately before application to a flexible sealing membrane (not shown).

In use the port of FIG. 7 operates in the same manner as the port of FIG. 6 whereby the vacuum in the wound cavity cause the sealing membrane and port to be pushed down by excess ambient air pressure onto a porous and resiliently compressible wound filling element to provide a direct path for wound exudate to the aspirant conduit as shown and described with reference to FIG. 5.

Although resiliently compressible wound filling elements have been described above it is only necessary for the wound filling element to remain porous when the maximum desired vacuum is applied and it is not necessary that it also be resiliently compressible. The air bleed port of FIG. 7 has the same advantages as does the port of FIG. 6.

FIG. 8 shows an air bleed port 700 which is generally suitable for use with the type of wound dressing as shown in FIG. 1. FIG. 8A shows a perspective view of the port; FIG. 8B shows cross section in elevation of the port of FIG. 8A; FIG. 8C shows a view in elevation of the port of FIG. 8A along the line 8C; FIG. 8D shows a top plan view of the port of FIG. 8A; and, FIG. 8E shows a cross section similar to that of FIG. 8B but with a portion of aspirant conduit inserted. The port 700 comprises an annular base flange portion 702 having a generally cylindrical wall portion 704 thereon. An angled tubular aspirant conduit receiving neck portion 706 supported on a bellows portion 708 is provided at the top of the wall portion 704. The wall portion 704 is provided with an air bleed hole 710 and a surrounding recess 712 to receive a filter element (not shown) as with other embodiments described above. The port 700 is moulded from a soft, flexible plastics material, the bellows portion 708 allowing the neck portion 706 to move and flex easily when an aspirant conduit 714 (see FIG. 8E) is in place. The port 700 may be used with the type of dressing shown in FIG. 1 where the aspirant conduit extends into the wound cavity 716 created between the wound bed and the sealing membrane 718. The end 720 of the conduit 714 may be associated with any desired item within the wound cavity such as a porous wound filling element whilst the other end 722 of the conduit 714 is connected to a waste canister and vacuum means (both not shown). The lower face 724 of the flange portion 702 is provided with an adhesive layer (not shown) to adhere to the sealing membrane 718 which has an aperture to coincide with an opening 730 in the annular base portion 702. The tubular neck portion 706 has an internal diameter to seal with the outer surface of the aspirant conduit 714.

In operation the wound cavity is evacuated to a desired pressure via the conduit 714 whilst a small but continuous air bleed through the hole 710 and filter in the recess 712 prevents wound exudate from stagnating due to a no-flow condition in the aspirant conduit 714. The flexible bellows portion 708 maintains the conduit 714 spaced-apart from the air bleed hole 710 thus preventing the hole from becoming blocked by the conduit surface due to the vacuum in the wound cavity.

As with previous embodiments the port 700 may be provided as a unit with a flexible sealing membrane by being adhered or welded thereto.

Figure 9A:
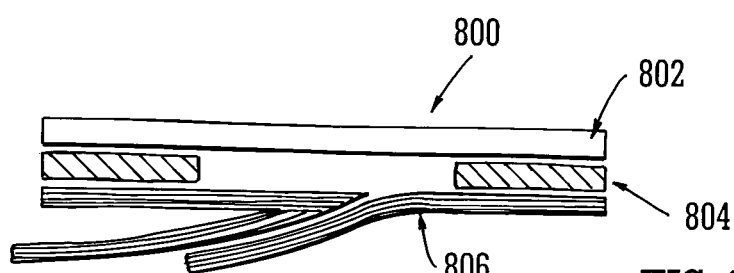
FIGS. 9A and 9B which show a cross section and plan view, respectively of a further embodiment of a port member according to the present invention.
Figure 9B:
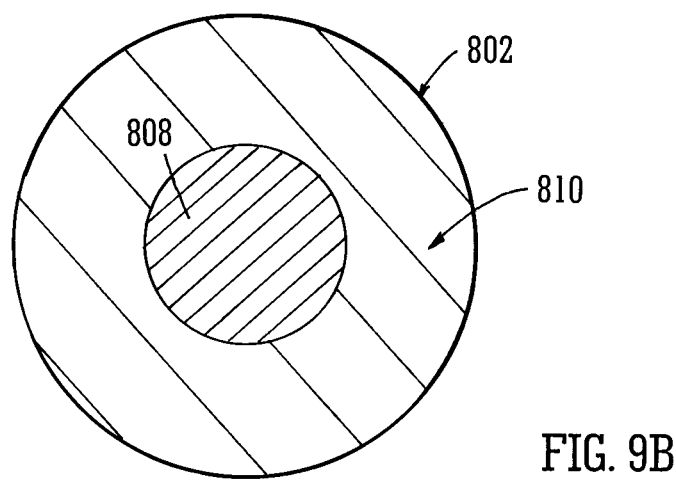

A further embodiment of an air bleed port member is shown in FIG. 9. The air bleed port member 800 comprises a patch of filter membrane 802 shown in FIG. 9B as circular (although it does not need to be round and could, for example, be rectangular) and having an annular layer of adhesive 804 applied to the outer periphery thereof, the adhesive being protected prior to use by protector papers 806. The adhesive layer prevents air bleed through that portion of the element which is coated with the adhesive. Therefore, by controlling the area of the filter membrane portion 810 coated with adhesive, the air bleed rate may be controlled through the uncoated portion 808 to an accurate level at a given pressure within a wound dressing. Thus, patches of filter membrane of a given size may be pre-coated with adhesive annuluses of varying widths or area allowing the user/clinician to choose the appropriate air bleed rate at the intended pressure.

Air bleed ports may be sterile packaged having an air bleed rate and associated pressure or pressure range printed thereon.

The air bleed port member of FIG. 9 may alternatively be pre-adhered or welded to a larger substrate layer of flexible sealing membrane as with other embodiments described above.

In the case of the port of FIG. 9 being welded to a flexible sealing membrane, the area of the filter membrane within the weld bead periphery would determine the air bleed flow rate. Thus, a range of air bleed port members welded to flexible sealing membranes may be prepared having different air bleed flow rates, the flexible sealing membrane having an aperture formed therein below the filter membrane portion through which air bleed occurs. In the case of the port being welded to a flexible sealing membrane the adhesive layer outside of the weld periphery may or may not be present.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A method of providing topical negative pressure therapy to a wound, comprising:
   positioning a topical negative pressure apparatus over a wound, the topical negative pressure apparatus comprising a port, the port comprising a partition positioned within a housing having a distal end located at an aperture and a proximal end, the partition extending at least partially over the aperture; and
   applying negative pressure to the wound.

2. The method of claim 1, wherein the topical negative pressure apparatus further comprises a connector.

3. The method of claim 2, wherein the connector comprises an air bleed.

4. The method of claim 1, wherein the negative pressure is provided by a vacuum pump.

5. The method of claim 1, wherein the negative pressure is applied via the aperture.

6. The method of claim 1, wherein the partition extends at least partially in a direction from the proximal end to the distal end.

7. The method of claim 1, wherein the partition extends from at least partially in a direction from a proximal wall to a distal wall of the housing.

8. The method of claim 1, wherein the port further comprises a second partition.

9. The method of claim 6, wherein the second partition is shorter than the first partition.

10. The method of claim 9, further comprising a plurality of partitions shorter than the first partition.

11. The method of claim 1, wherein the port comprises a base portion.

12. The method of claim 11, wherein the base portion is configured to adhere to a sealing membrane.

13. The method of claim 11, wherein the base portion comprises an adhesive.

14. The method of claim 11, wherein the base portion defines a flange and comprises a planar lower surface.

15. The method of claim 3, wherein the air bleed comprises an aerification orifice.

16. The method of claim 15, wherein the air bleed comprises a filter element at the aerification orifice.

17. The method of claim 1, wherein the housing comprises a soft, flexible material.

18. The method of claim 1, wherein the partition is configured to taper along the length of the partition.

19. The method of claim 2, wherein the connector is within a fluid path between the port and a source of negative pressure.

20. The method of claim 4, wherein the vacuum pump is configured to be connected to the port via a conduit.

* * * * *